United States Patent
Xue et al.

(10) Patent No.: US 7,081,567 B2
(45) Date of Patent: Jul. 25, 2006

(54) TRANSGENIC DUNALIELLA SALINA AS A BIOREACTOR

(75) Inventors: Lexun Xue, 40 Daxue Road, Zhengzhou, Henan, 450052 (CN); Weidong Pan, Henan (CN); Guozhong Jiang, Henan (CN); Jianmin Wang, Henan (CN)

(73) Assignees: Lexun Xue, Henan (CN); Zhengzhou University, Henan (CN)

( * ) Notice: Subject to any disclaimer, the term of this patent is extended or adjusted under 35 U.S.C. 154(b) by 404 days.

(21) Appl. No.: 09/997,445

(22) Filed: Nov. 29, 2001

(65) Prior Publication Data

US 2003/0066107 A1    Apr. 3, 2003

(30) Foreign Application Priority Data

Dec. 3, 2000   (CN) ................. 00 1 31217
Sep. 21, 2001  (CN) ................. 01 1 28486

(51) Int. Cl.
  *A01H 1/00*  (2006.01)
  *A01H 5/00*  (2006.01)
  *C12N 15/82* (2006.01)
  *C12N 15/87* (2006.01)

(52) U.S. Cl. ............ 800/288; 800/292; 800/293; 800/300; 800/295; 435/320.1; 435/419; 435/468; 435/470; 536/23.1

(58) Field of Classification Search ........... 800/295, 800/300, 288, 292, 293; 536/23.1; 435/419, 435/320.1, 468, 470
See application file for complete search history.

(56) References Cited

U.S. PATENT DOCUMENTS 5,612,487 A    3/1997   Lam et al. ............. 800/205
6,000,551 A   12/1999   Kanel et al. ........... 209/164
6,194,560 B1   2/2001   Arntzen et al. ......... 536/23.7
6,307,123 B1  10/2001   Kriz et al. ............ 800/282
6,358,507 B1   3/2002   Kaplan et al. .......... 424/93.2

OTHER PUBLICATIONS

Chasen (Plant Cell, vol. 4, pp. 1-2, 1992, p. 1).*
(Hansen et al., 1999, Trends in plant Science, vol. 4, pp. 226-231, see p. 230).*
Porath, et al. (Developing a transformation system for Dunaliella, 1997, Phycologica, vol. 36, No. 4 SUPPL, p. 89, Meeting information: Sixth International Phycological Congress. Leiden Aug. 9-16, 1997).*
Mason, H.S. et al., *Proc. Natl. Acad. Sci, USA*, 1992, 89:11745-11749.
Thanavala, Y. et al., *Proc. Natl. Acad. Sci. USA*, 1995, 92:3358-3361.
Kong, Q et al., *Proc. Natl. Acad. Sci. USA*, 2001, 98:11539-11544.
Fisher, M. et al., *J. Biol. Chem.*, 1997, 272:1565-1570.
Schroda, M. et al., *The Plant Journal*, 21(2):121-Jan. 2000.

* cited by examiner

*Primary Examiner*—Elizabeth McElwain
*Assistant Examiner*—Georgia Helmer
(74) *Attorney, Agent, or Firm*—Morgan & Finnegan, LLP (57) ABSTRACT

Disclosed is a method for making a bioreactor comprising a foreign target gene, special selectable markers and Dunaliella Salina as host. It is prepared by the genetic transformation techniques that include introducing a foreign target gene into the cells of Dunaliella Salina and screening the transformed cells of Dunaliella Salina. The bioreactor of the present invention can be used as a safe and cheap production system for proteins of pharmaceutical interest including vaccines, especially oral products, in a large scale, because the cells of Dunaliella Salina are easy of genetic manipulation in preparation of the bioreactor, nontoxic and edible for humans and animals, and harmless to the environment.

3 Claims, 5 Drawing Sheets

TRANSGENIC DUNALIELLA SALINA AS A BIOREACTOR

FIELD OF THE INVENTION

The present invention relates to a bioreactor, preparation and use thereof, more particularly, this invention relates to a transgenic Dunaliella Salina bioreactor, preparation and use thereof.

BACKGROUND OF THE INVENTION

It is well known that vaccines administered to humans and animals can induce their immune systems to produce antibodies against many pathologic organisms, such as viruses and bacteria. For example, vaccines containing the given antigens, such as hepatitis B surface antigen (HBsAg), human measles virus antigen, malaria antigen, foot-and-mouth disease virus antigen, rabies virus antigen, etc., are important measures to prevent and control such infectious diseases as hepatitis B, measles, malaria, foot-and-mouth disease and rabies in humans or animals. The traditional vaccines are produced from killed or live attenuated pathogens. Recently, several academic and industrial laboratories have begun experimenting with transgenic microorganisms, plants or animals as novel manufacturing systems. However, the applications of these methods are limited greatly for their intrinsic defects which follow: a) some microorganism expression systems lack post-translational modifications, for example, protein glycosylation to eukaryotic proteins. Some insoluble aggregates, for which to be re-dissolved is very difficult, often emerge during fermentation of *Escherichia coli*. In addition, a huge investment of equipments is often required for the fermentation; b) a high cost is required for culturing animal cells, and what is more serious is that the recombinant proteins produced by transgenic animals may be contaminated with pathogenic viruses from animals, which may be a potential danger to humans.

At present, for example, the hepatitis B vaccine used clinically consists of major protein particles of HBsAg expressed mainly by *Saccharomyces cerevisiae*. Although the vaccine is effective and plays an important role in controlling transmission of hepatitis B virus, it still has many shortcomings, such as low or no reactivity to some people, immune escape after inoculation, and high price which prevents itself from using widely in the developing countries. Hence, the development of a more effective, and cheaper hepatitis B vaccine is significant for world-widely controlling hepatitis B virus infection.

As compared with other production systems such as microorganism fermentation and transgenic animals, plant as a bioreactor for producing pharmaceutical proteins is safer and cheaper due to the following reasons: firstly, plant viruses do not infect humans, so it is safer; secondly, neither expensive culture materials nor complicated equipments are needed for culture of plant cells; finally, strictly aseptic production conditions and a cold storage can be omitted during distributing.

The biomedical studies on transgenic plants have been made since 1990's. For example, the expression of HBsAg in tobacco was successfully demonstrated in 1992, and later many studies were carried out on some edible plants including tomato, lupine, lettuce, etc. The studies mentioned above have shown that these plants can express human hepatitis B surface antigen protein, but the yield of protein is low. These plants are not often eaten in raw due to seasonal growth thereof. Therefore, it is difficult for them to be adopted widely among the population, especially children in which hepatitis B virus infection is a major health problem.

Hence, it is an objective of the present invention to provide a new and effective transgenic Dunaliella salina bioreactor, which can be used to produce many valuable pharmaceutical proteins including vaccines for humans and/or animals.

It is another objective of the present invention to provide a method for preparing the transgenic Dunaliella Salina bioreactor which is used to produce pharmaceutical proteins, vaccines and hormones suitable for humans, animals and plants.

Unless indicated otherwise, the term "Dunaliella Salina" refers to a kind of organism classified as Chlorophyta; Chlorophyceae; Volvocales; Dunaliellaceae. Dunaliella Salina is, in the shape of pear or ellipse with volume of 50~1000 $\mu m^3$, the most halotolerant unicellular eukaryotic organism known. The cell of Dunaliella Salina has two long apical flagella that propel it through the water. The significant difference between Dunaliella Salina and other green unicellular algae is that the cell of Dunaliella Salina lacks a rigid cell wall, and is enclosed by a thin layer of elastic plasma membrane. In the cell, there is the single, large, cup-shaped chloroplast with a pyrenoid. The red eyespot is located at the front end of the cell. Reproduction of Dunaliella Salina thereof includes asexual reproduction in longitudinal split as the main manner and sexual reproduction in isogamy.

The term "transgene", as used herein, refers to a foreign double-stranded deoxyribonucleic acid (DNA) fragment introduced into Dunaliella Salina as host, which can be either extrachromosomal or integrated into the host genome, and the resulting transgenic Dunaliella Salina can be propagated by normal breeding or not.

The term "foreign target gene" refers to the DNA sequence introduced into the host Dunaliella Salina, which encodes a protein or peptide product.

The term "bioreactor" refers to the transgenic animals, plants or microorganism, which can be used to produce the proteins or peptides encoded by the introduced foreign genes.

The term "selectable marker" refers to the DNA sequence encoding special protein or peptide products, and the host carrying such a sequence can grow, propagate and be screened in a special selective medium.

SUMMARY OF THE INVENTION

On the basis of the findings from repeated and detailed studies in our laboratory, the present inventors have developed a new and effective Dunaliella Salina bioreactor that can be prepared by introducing foreign target genes derived from humans, animals, plants or microorganisms into the cells of Dunaliella Salina using the well-known genetic transformation techniques, incl polyethylene glycol (PEG) and gene-gun, and then screening the transformed cells. The bioreactor can be used to produce many cheap drugs, vaccines, phytohormones and other bioactive materials for humans or animals, therefore, can fulfill the purposes of the present invention.

The present invention provides a transgenic Dunaliella Salina bioreactor comprising a Dunaliella Salina as host, a foreign target gene and a selectable marker.

In one preferred embodiment of the present invention, the said foreign target gene is derived from at least one selected from the group consisting of humans, animals, plants or microorganisms.

In a further embodiment of the present invention, the said selectable marker is at least one selected from the group consisting of spectinomycin or streptomycin resistance encoded by aadA gene, chloromycetin resistance encoded by cat gene, kanamycin or neomycin resistance encoded by nptII or neo gene, hygromycin resistance encoded by hyg gene and PPT resistance encoded by Bar gene.

Further, the present invention also provides a method for preparing the transgenic Dunaliella Salina bioreactor, which comprises:
   a) Introducing foreign target genes into the cells of Dunaliella Salina with the transformation techniques;
   b) Screening the transformed cells of Dunaliella Salina.

The present invention further provides the uses of the transgenic Dunaliella Salina bioreactor in production of the vaccines for humans and/or animals.

DETAILED DESCRIPTION OF THE INVENTION

The present invention provides a transgenic Dunaliella Salina bioreactor comprising a foreign target gene, a selectable marker and a Dunaliella Salina as a host.

The use of Dunaliella Salina as the host, as in the present invention, is considered to have significant advantages due to the following reasons: Dunaliella Salina is probably the most halotolerant unicellular eukaryote known, and can grow in high salinity environments, such as oceans or brine lakes, etc. The cell of Dunaliella Salina has no cell wall, which permits rapid volume changes in adaptation to extracellular changes in osmotic pressure. As a result, its adaptability to the environments is extremely strong, and can live in a variety of salt concentration from as low as 0.2% to salt saturation concentration (35%). Dunaliella Salina has a strong capability of photosynthesis and can synthesize many organic molecules like proteins from water, carbon dioxide and inorganic salts under sunlight. For this reason it is easy and cheap to culture the cells of Dunaliella Salina.

As in one preferred embodiment of the present invention, the said foreign target gene is derived from at least one selected from the group consisting of humans, animals, plants or microorganisms, which can be either cloned from any genomes from above-mentioned organisms, artificially synthesized or amplified by polymerase chain reaction (PCR) in vitro.

The examples of the said foreign target gene derived from microorganisms and plants includes but not limited to HbsAg, measles virus antigen, foot-and-mouth disease virus antigen, rabies virus antigen, larvacide, cytokinin, endochitinase, glucose-amylase P, thaumatin, seed-stored protein genes, and the like.

The examples of the said foreign target genes derived from humans and animals include but not limited to angiostatin, endostatin, hemoglobin, human factor III, human erythropoietin, interferon, obese protein, human interleukin, human granulocyte colony stimulating factor, human macrophage colony stimulating factor, streptokinase, human protein kinase, growth hormone, tissue plasminogen activator, defensin, tumor necrosis factor, epidermal growth factor, bovine chymosin, antibiotic peptide genes, and the like.

All of these foreign target genes listed above can be used individually to construct at least one expression vector from the group consisting of Dunaliella Salina genome expression vectors, chloroplast expression vectors, and autonomously replicating expression vectors.

As in a further preferred embodiment of the present invention, the said selectable marker is at least one selected from the group consisting of spectinomycin or streptomycin resistance encoded by aadA gene, chloromycetin resistance encoded by cat gene, kanamycin or neomycin resistance encoded by npt II or neo gene, hygromycin resistance encoded by hyg gene and PPT resistance encoded by Bar gene.

Further, the present invention provides a method for preparing the transgenic Dunaliella Salina bioreactor, which comprises:
   a) introducing foreign target genes into the cells of Dunaliella Salina using the transformation techniques.
   b) screening transformants of Dunaliella Salina.

As noted above, the said transformation techniques in step a) can be any one of the methods for genetic transformation consisting of biological, physical or chemical methods. Specifically, the foreign target gene can be introduced into the cells of Dunaliella Salina by either biological, physical or chemical methods for genetic transformation techniques, and then be expressed in the transformed cells of Dunaliella Salina.

The said biological method can be such a method that foreign target genes are introduced into the cells of Dunaliella Salina by either agrobacterium Ti plasmid transformation system or plant virus vector system, and then expressed in the transformed cells of Dunaliella Salina.

The said physical and chemical methods can be one or more of the following methods:
   a. introducing foreign target genes into the cells of Dunaliella Salina by PEG treatment and expressing them;
   b. introducting foreign target genes into the cells of Dunaliella Salina by liposome and expressing them;
   c. introducing foreign target genes into the cells of Dunaliella Salina by electroporation and expressing them;
   d. introducing foreign target genes into the cells of Dunaliella Salina by ultrasonic delivery and expressing them;
   e. introducing foreign target genes into the cells of Dunaliella Salina by gene gun and expressing them;
   f. introducing foreign target genes into the cells of Dunaliella Salina by microinjection and expressing them;
   g. introducing foreign target genes into the cells of Dunaliella Salina by ultraviolet laser microbeam and expressing them;
   h. introducing foreign target genes into the cells of Dunaliella Salina by glass bead agitation and expressing them;
   i. introducing foreign target genes into the cells of Dunaliella Salina by aerosol gene delivery and expressing them;

According to one preferred embodiment of the present invention, the process used in the invention further comprises a procedure of constructing Dunaliella Salina expression vector and a procedure of culturing Dunaliella Salina before introducing foreign target genes into Dunaliella Salina cells.

In another preferred embodiment of the present invention, the method for preparing the transgenic Dunaliella Salina bioreactor of the present invention comprises the following steps which were illustrated with an example of the transgenic Dunaliella Salina expressing HBsAg.
- a) constructing the CtxB-SS1 fusion gene encoding recombinant HbsAg;
- b) constructing the Dunaliella Salina expression vector pCAMBIA-CtxB-SS1 containing the said fusion gene in step a);
- c) introducing the said expression vector in step b) into the cells of Dunaliella Salina;
- d) selective subculture;
    - wherein the said recombinant HBsAg-encoding gene includes all or part of the sequences of S, PreS1 and PreS2 genes of hepatitis B virus, and combinations thereof; SS1 gene herein refers to the fusion of sequences of S and PreS1 genes; the CtxB-SS1 fusion gene herein refers to the fusion of cholera toxin B subunit (CtxB) and SS1 genes.

In one preferred embodiment of the present invention, the CtxB-SS1 fusion gene was inserted between the Dunaliella Salina Hsp70B 5' promoter and the T-Nos terminator to construct an intact expression cassette for transcription of the CtxB-SS1 fusion gene under the control of the Dunaliella Salina Hsp70B 5' promoter.

In a further preferred embodiment of the present invention, the said expression vector pCAMBIA-CtxB-SS1 contained two sequences of matrix attachment regions (MAR), MAR1 and MAR2, in the same orientation. The expression cassette of Nit1 5'-Nit1-T-Nos expressing nitrate reductase was inserted between MAR1 and MAR2 to screen the transformed Dunaliella Salina.

The present invention also provides the uses of the bioreactor in production of vaccines for humans or animals. The transgenic Dunaliella Salina bioreactor of the present invention can be used to prepare or produce human or animal vaccines containing the following antigens, such as HBsAg, influenza hemagglutinin, malaria antigen, measles virus antigen, rabies virus antigen, foot-and-mouth disease virus antigen, phytohormones, and the like.

It is believed that, as compared with other transgenic bioreactors, the transgenic Dunaliella Salina bioreactor of the present invention possesses many advantages:
1. Dunaliella Salina is a unicellular organism and its protein content is higher. The alga propagates very fast and grows without seasonal restriction, and it can grow to dense populations in a shorter time, which allows it easy to screen the transformed Dunaliella Salina.
2. Dunaliella Salina is a lower eukaryotic green alga lacking of cell wall, therefore genetic manipulation thereof is easier. In addition, there is the single, large, cup-shaped chloroplast in the cell, which is useful for the chloroplast transformation of foreign genes. The chloroplast transformation is harmless to the environments and does not induce gene silencing.
3. The cultivation of Dunaliella Salina is based on autotrophic growth in media containing inorganic salts, e.g. nitrate as the nitrogen source and carbon dioxide as the exclusive carbon source, so the cost of the culture is low. Dunaliella Salina can grow in the high salinity media which other organisms cost of production can be decreased greatly because two models of cultivation, intensive and extensive, have been used in the large-scale cultivation of Dunaliella Salina.
4. Dunaliella salina has the eukaryotic post-translational processing for proteins, such as the formation of disulfide bond and glycosylation, which simplifies processing of the downstream of gene engineering and assures bioactivity and quality of the protein products.
5. Dunaliella Salina is, because of being nontoxic and abundant in natural vitamins and polyunsaturated fatty acids, valuable edible alga. Oral vaccines or drugs produced with Dunaliella Salina can be taken directly even without purification, so that the cost of production may be reduced markedly.
6. The bioreactor system according to the present invention may be used to produce drugs or vaccines for humans and/or animals, phytohormones and other bioactive materials.

Further description is given with the examples which follow, and these examples are provided for the purposes of illustration and are not intended to limit the scope of the present invention.

EXAMPLES

Example 1

I. Culture of Dunaliella Salina
   The strain and culture conditions are as follows.
   1. Liquid culture: Dunaliella Salina UTEX1644 was obtained from The Culture Collection of Algae at The University of Texas at Austin, and inoculated into Mclachlan culture fluid. In liquid culture, the cells of Dunaliella Salina UTEX1644 were cultured at temperature of 20–30° C. in the flasks and under 14:10-hour light-dark cycle with 3000 lux.
   2. Solid culture: Agar was added into Mclachlan culture fluid up to 0.5–0.8% to prepare solid media. The alga cells being isolated from the liquid culture were transferred immediately onto the solid media prepared above by use of aseptic technique, and then cultured under the same conditions as liquid culture.

II. Construction of the chloroplast expression vector p64C-TNF-AAD of TNF
   1. The Vector pSK-atpX contains cloned chloroplast atpA 5' promoter sequence and rbcL 3' terminator sequence. Therefore, the said inserted foreign gene can be expressed highly in the chloroplast. The plasmid pUC19-TNF contains a cDNA fragment of human tumor necrosis factor (referred to as TNF-α hereinafter), which is about 600 bp in length and has a BamH I site at one end and a Xba I site at the other end. The cDNA fragment of TNF-α was inserted between the atpA5' promoter sequence and the rbcL 3' terminator sequence after the vector pSK-atpX and the plasmid pUC19-TNF were digested with BamH I and Xba I, and then an intermediate vector pSK-atpK-TNF containing the expression cassette of human TNF-α gene (atpA5'-TNF-rbcL3') was constructed.
   2. The vector p64C contains cloned homologous fragment to the chloroplast of Dunaliella Salina, clpP-trnl-petB, as well as the 5' promoter and 3' terminator sequences of the chlL gene. Both the vector p64C and the intermediate vector pSK-atpX-TNF prepared in step 1 were digested with EcoR V and Sac I, and then the obtained expression cassette of TNF-α gene was inserted into vector p64C to construct the chloroplast intermediate expression vector p64C-atpX-TNF. Wherein the said expression cassette of TNF-α gene was located in the downstream of both promoters chlL and atpA, which can strengthen expression of the TNF-α gene.

Figure 1:
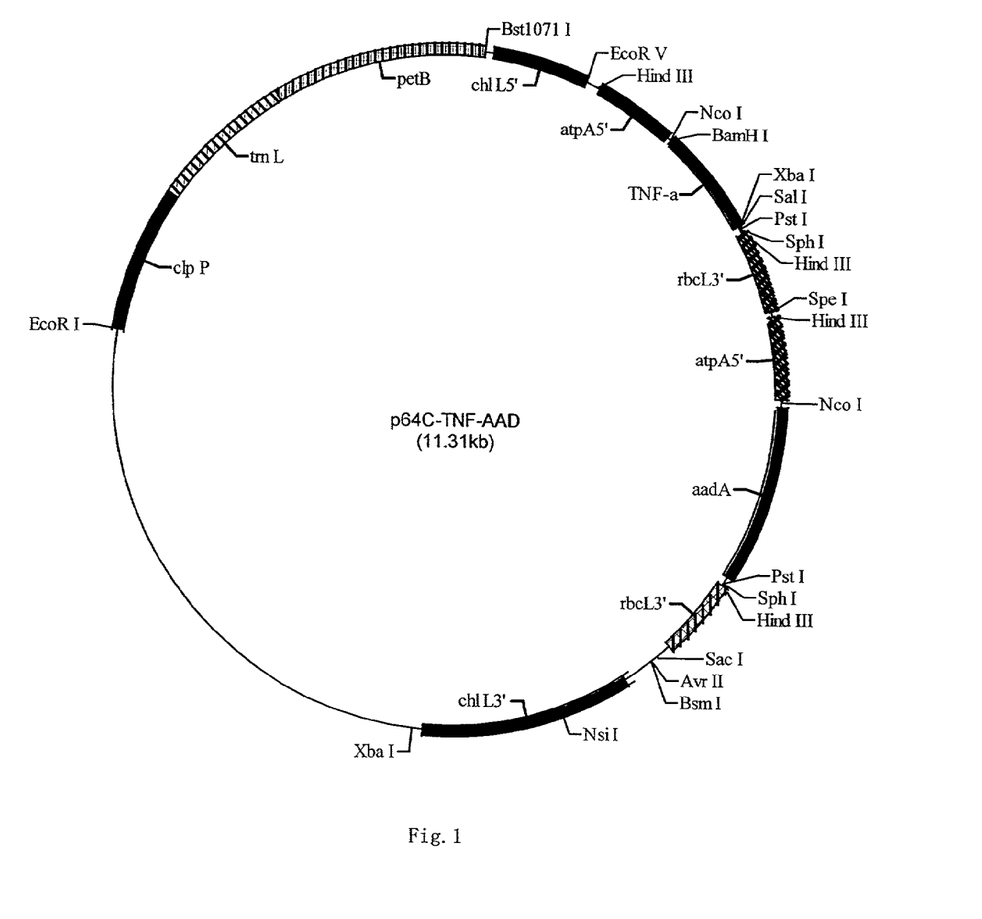
FIG. 1 shows a schematic diagram of the chloroplast expression vector p64-TNF-AAD containing tumor necrosis factor (TNF).

3. On the vector pUC-atpX-MD, there is the cloned expression cassette of aadA gene, atpA5'-aadA-rbcL3', which can express aminoglycoside-3'-adenylate transferase (i.e. spectinomycin resistance selectable marker). The vector pUC-atpX-AAD was digested with EcoR V and Sac I, then a 1.9 kb expression cassette of aadA gene was obtained. The chloroplast intermediate expression vector p64C-atpX-TNF prepared in step 2 was filled to blunt ends using $T_4$ DNA polymerase after digestion with Not I, subsequently, digested with Sacl, and finally inserted into p64C-atpX-TNF to construct the chloroplast expression vector p64C-TNF-AAD (FIG. 1), which contained the expression cassette of human TNF-α gene (atpA5'-TNF-rbcL3') and the expression cassette of aadA gene (atpA5'-aadA-rbcL3'). The expression cassette of TNF-α gene was directly located in the downstream of the chlL5' promoter, which strengthens its expression under the control of the both promoters chlL and atpA. Furthermore, the expression cassette of aadA gene can express spectinomycin resistance, which is helpful for screening the recombinants of Dunaliella Salina.

III. Introducing Foreign Target Genes into the Cells of Dunaliella Salina

1. Introducing Foreign Target Genes into the Cells of Dunaliella Salina by Electroporation The cells of Dunaliella Salina cultured in fluid medium for 5 days were centrifuged at 1000 rpm for 15 min, and the supernatant was discarded. After treatment with the solution containing 0.2M mannite and 0.2M sorbitol, the cell density of Dunaliella Salina was adjusted to $10^8$/ml by adding Buffer A (0.5 M $CaCl_2$ in 0.1 M Tris, final pH 7.2.). After the plasmid containing the foreign gene at a final concentration of 10 μg/ml and salmon sperm DNA at a final concentration of 25 μg/ml were mixed well, the mixture was placed on ice for 5–10 min, and then 0.5 ml of cooled mixture was transferred into 0.2 cm electrode gap cuvette. The electroporation was performed at an electrical condition of 2.6 KV/cm field strength, 200 ohms resistance, and 25 μF capacitance, corresponding to a time range of 5–10 msec, using a Gene Pulser II system (Bio-Rad). Following delivery of the electrical pulse, 0.5 ml Buffer A was added to the suspension and kept on ice for 10 min, and the "clump" of cells was gently shaken to disperse into small pieces. Finally, the treated cells of Dunaliella Salina were cultured under the conditions suitable for their growth.

2. Introducing Foreign Target Genes into the Cells of Dunaliella Salina with Gene Gun The cells of Dunaliella salina cultured for 5 days in liquid medium were centrifuged at 1000 rpm for 15 min. Subsequently, the supernatant was discarded and the cell density of Dunaliella Salina was adjusted to $10^8$/ml with Dunaliella Salina liquid medium, and then 0.5 ml of the cells was smeared in the center of the solid medium plate on a circle of about 3 cm in diameter and finally was blown dry under aspectic condition for further use.

For microprojectile bombardment, prewashed 50 μl aliquots of gold powder suspension (60 μg/ml) were coated with 6 μg of plasmid containing the foreign gene on ice. Fifty μl sterile aliquots of 2.5M $CaCl_2$ and 20 μl of 0.1M spermidine were added to the above-mentioned mixture containing DNA particles, and mixed in a microfuge tube (1.5 ml). The resulting mixture was vortexed for 3 min at room temperature and centrifuged at 12000 rpm for 10 sec. After the supernatant was removed, the DNA particles were washed twice with 240 μl absolute ethanol and re-suspended in 60 μl absolute ethanol. Subsequently, 6–8 μl of the suspension was spread onto the center of each macrocarrier and air-dried.

Bombardments were performed using the PDS-1000 helium-driven biolistics particle delivery system (Bio-Rad). Each plate was bombarded 3 times at a rupture pressure of 600 psi, and then cultured under the conditions suitable for the growth of the cells of Dunaliella Salina.

3. Introducing Foreign Target Genes into the Cells of Dunaliella salina with PEG-Mediated Transformation The protoplasts of Dunaliella Salina were prepared with 0.5 ml alga culture (cell density of $10^7$–$10^8$/ml). After 1 μg of carrier DNA (calf thymus DNA) and 5–10 μg of plasmid DNA containing the foreign gene were mixed and gently swirled, the newly prepared suspension of the protoplasts was incubated at room temperature for 20 min. One ml solution of PEG (MW4000–6000) was added to the suspension of the protoplast mentioned above, swirled, and then again incubated at room temperature for 10 min to boost the protoplast to take up DNA. The transformed protoplast was collected with centrifugation at 1000 rpm for 15 min, re-suspended in 2 ml solution of 1 M sorbitol, and cultured under the conditions suitable for the growth of Dunaliella Salina.

IV. Screening the Transformants of Dunliella Salina

The cells of Dunaliella Salina transformed with electroporation, gene gun or PEG were inoculated onto the solid media containing proper screening reagent(s). Under proper culture conditions, Dunaliella Salina colonies would emerge 2–4 weeks later. These colonies were cultured in the liquid media having no antibiotic for 3–5 days, and then screened for the second time on the solid media containing antibiotic. After being sub-cultured for more than 10 times, these transformants were growing luxuriantly.

Example 2

I. Dunaliella Salina Culture

The same culture used as described in example 1.

Figure 2A:
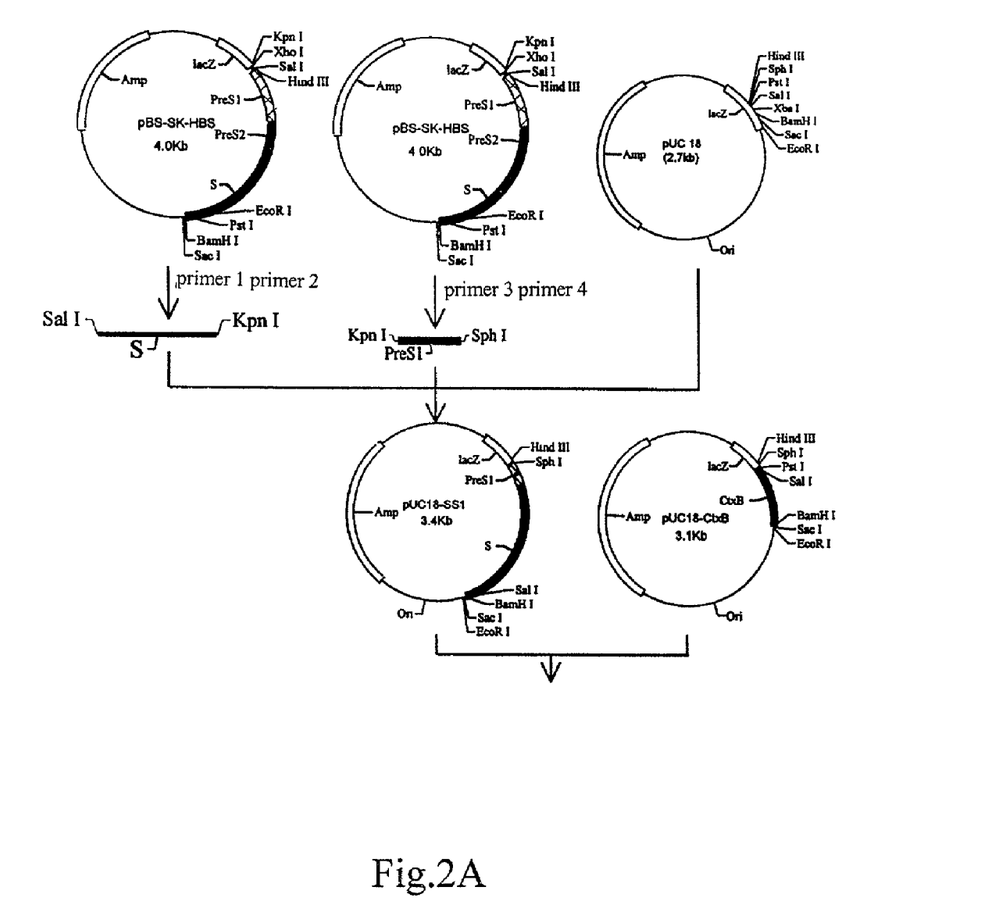
FIG. 2A and FIG. 2B illustrate the construction of the Dunaliella Salina expression plasmid pCAMBIA-CtxB-SS1 containing recombinant HB
Figure 2B:
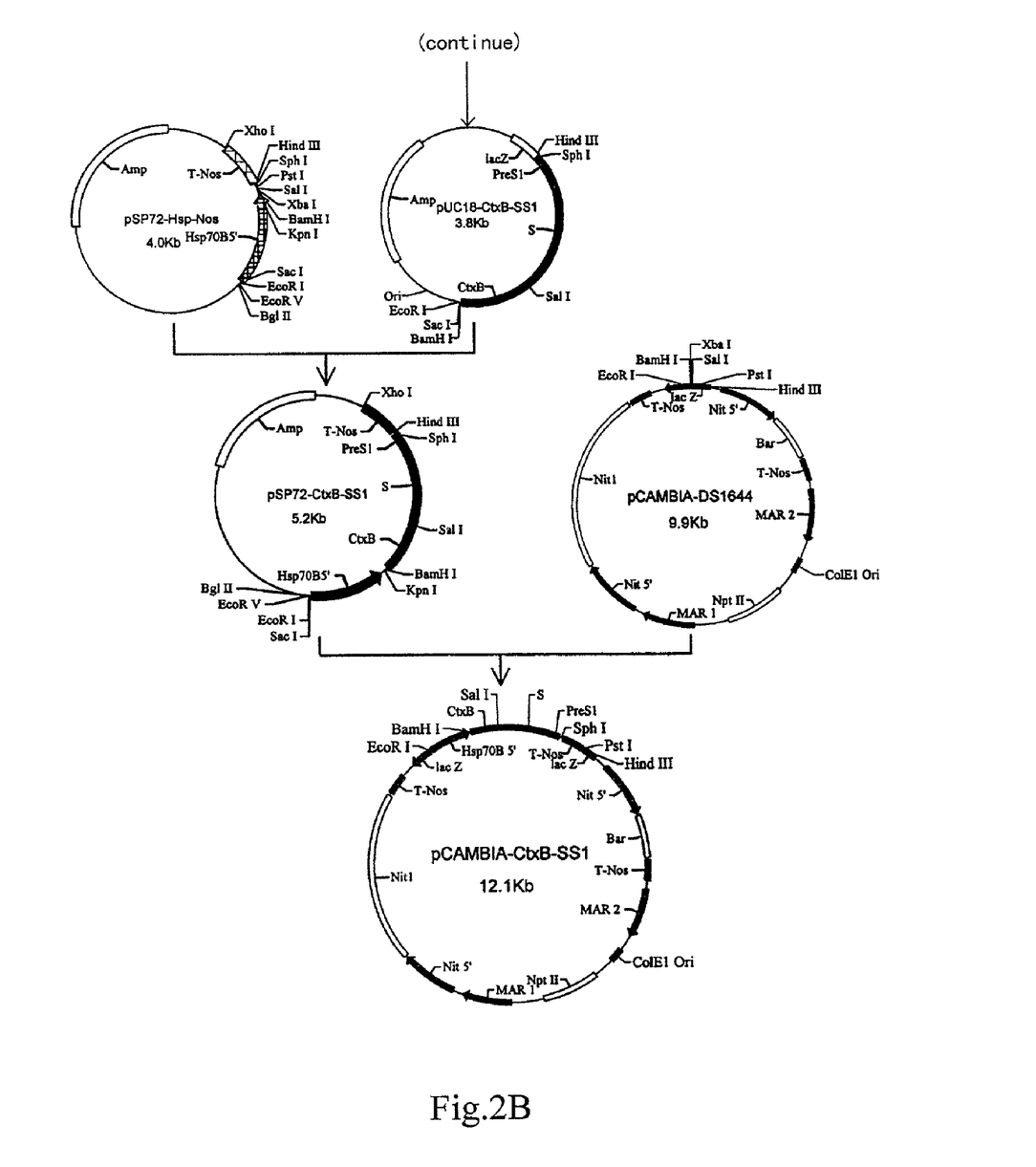

II. Construction of the Dunaliella Salina Expression Plasmid pCAMBIA-CtxB-SS1 encoding recombinant HbsAg (FIG. 2).

1. Construction of the Recombinant HBsAg SS1 Fusion Gene

Plasmid pBS-SK-HBS contained sequences of S, Pre-S2 and Pre-S1 genes of hepatitis B virus. Four primers for amplification of the genes listed above were designed as follows:

```
Primer 1:   5'-GCAGTCGACCCAATG GAGAGCAC-3';
                Sal I

Primer 2:   5'-GCGGGTACCAGG AATGTATACCC-3';
                Kpn I

Primer 3:   5'-CTGGGTACCCCA AATCCTCTGGG-3';
                Kpn I

Primer 4:   5'-GCGGCATGCTTA GTTGGGGTTG-3';
                Sph I
```

The S gene fragment encoding 1–226 amino residues of HBsAg and the PreS1 gene fragment encoding 20–48 amino residues of PreS1Ag were amplified using primers 1 and 2, and primers 3 and 4, respectively. After restriction enzyme digestion and recovery, the two fragments were ligated at the Sal I /Sph I site in the plasmid pUC18 to construct a new plasmid named pUC18-SS1, which contains the fusion gene SS1 encoding recombinant hepatitis B surface antigen comprising 1–226 amino residues of HBsAg and 20–48 amino residues of PreS1Ag.

2. Construction of CtxB-SS1 Fusion Gene (1) A pair of primers was designed according to the cholera toxin B subunit gene sequence reported.

```
Forward primer:
5'-GCGGGATCCATG ATTAAATTAAAATTTGG-3';
       BamH I

Reverse primer:
5'-GCGGTCGACAGG ATTTGCCATACTAATTGC-3';
       Sal I
```

When the genomic DNA of *Vibrio cholerae* (O139) was used as a template for PCR, a CtxB gene of 380 bp was obtained by PCR amplification, and then the CtxB gene was cloned into plasmid pUC18 after digestion with BamH I/Sal I to construct a new plasmid pUC18-CtxB.

(2) A SS1 fusion gene of 770 bp in length was obtained after digestion of plasmid pUC18-SS1 with Sal I/Sph I, and then ligated at the Sal I/Sph I site in plasmid pUC18-CtxB to construct plasmid pUC18-CtxB-SS1 which contains the CtxB-SS1 fusion gene consisting of CtxB and SS1 genes.

3. Construction of Hsp70B 5'-CtxB-SS1-T-Nos Expression Cassette

Plasmid pSP72-Hsp-Nos contained heat shock protein Hsp70B 5' promoter of Dunaliella Salina and T-Nos terminator. Both plasmid pSP72-Hsp-Nos and plasmid pUC18-CtxB-SS1 were digested with BamH I/Sph I, and then the CtxB-SS1 fusion gene was ligated between the Hsp70B 5' promoter and the T-Nos terminator to construct a new plasmid pSP72-CtxB-SS1 containing an intact expression cassette in which the CtxB-SS1 fusion gene transcribes under the control of Hsp70B 5' promoter.

4. Construction of Expression Plasmid pCAMBIA-CtxB-SS1 of Dunaliella Salina

Figure 3:
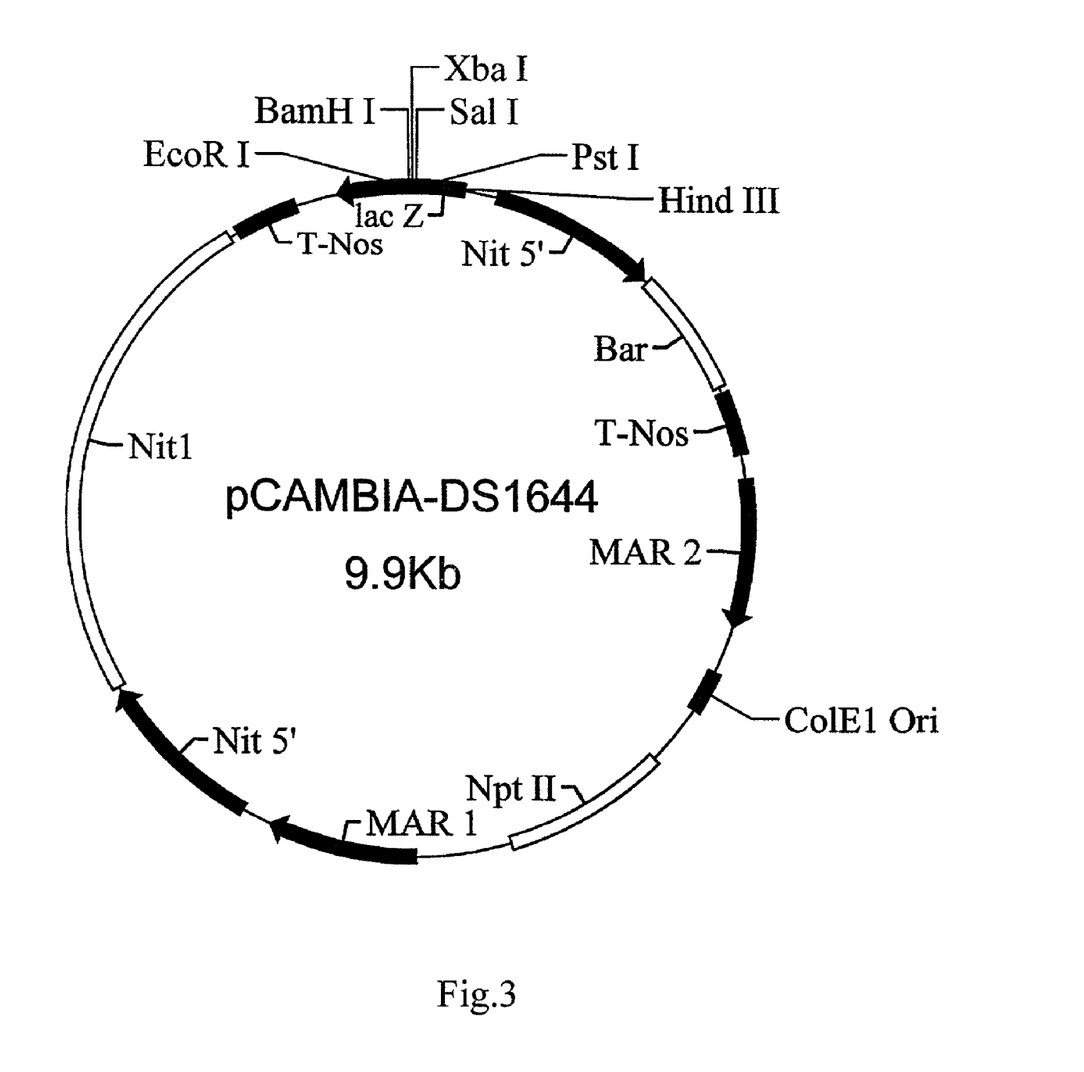
FIG. 3 is a schematic diagram of the Dunaliella Salina expression vector pCAMBIA-DS1644.
Figure 4:
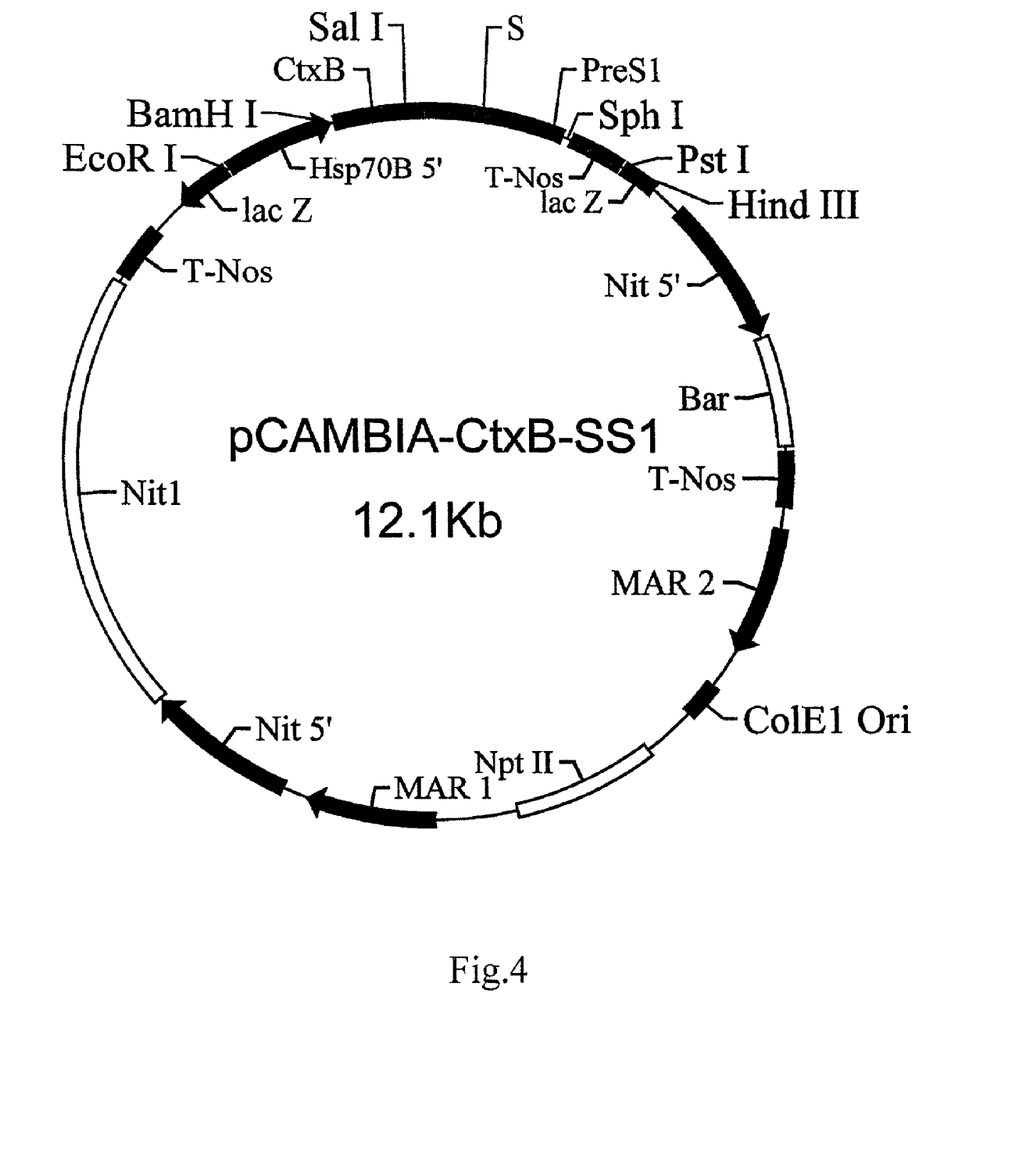
FIG. 4 is a schematic diagram of the Dunaliella Salina expression plasmid pCAMBIA-CtxB-SS1 containing recombinant HBsAg.

There were two matrix attachment regions (MAR) with the same orientation, MAR1 and MAR2, in Dunaliella Salina expression vector pCAMBIA-DS1644 (FIG. 3). Between MAR1 and MAR2, the following elements were linked in sequence:(a) the expression cassette of Nit5'-Nit1-T-Nos, which can express nitrate reductase used to screen the transgenic Dunaliella Salina, (b) a multiple cloning site MCS derived from pUC18, and (c) the expression cassette of Nit5'-BAR-T-Nos, which expresses a PPT resistance used as an assistant screening. An intact expression cassette of Hsp70B5'-CtxB-SS1-T-Nos was acquired by digestion of plasmid pSP72-CtxB-SS1 with EcoR I/Xho I and was ligated at EcoR I/Sal I site in plasmid pCAMBIA-DS1644 to construct expression plasmid pCAMBIA-CtxB-SS1 (FIG. 4). Homologous recombination mediated by MAR1 and MAR2 can take place, which makes the expression cassettes, including Nit1, CtxB-SS1 and BAR, integrated to the active transcription region of the Dunaliella Salina chromosome. After being screened by the PPT resistance and by the nitrate selective culture, the transformed Dunaliella Salina would highly express the fusion protein of CtxB and SS1 induced by changes of temperature.

III. Introducing Foreign Target Genes into the Cells of Dunaliella Salina

1. Introducing Foreign Target Genes into the Cells of Dunaliella Salina with Electroporation The same introduction as described in example 1.

2. Introduction Foreign Target Genes into the Cells of Dunaliella Salina with Gene Gun The same introduction as described in example 1.

3. Introducing Foreign Target Genes into the Cells of Dunaliella Salina with PEG The same introduction as described in example 1.

IV. Screening the Transformants of Dunaliella Salina

The cells of Dunaliella Salina transformed with electroporation, gene gun or PEG, etc., were washed with 1 ml culture fluid A containing 5 mM NH$_4$Cl, 5 mM NaNO$_3$, cultured for 2–3 days with 300 lux, and then inoculated into culture fluid A containing 3 μg/ml PPT. After the transformed cells were cultured for 5–7 days under the following conditions: 12:12 light-dark cycle with 1600 lux, they were again inoculated into culture fluid B containing 10 mM NaNO$_3$ and cultured for 7–10 days. At last, the cells were smeared onto the solid media that were made up of culture fluid B and agar, and continued to culture for 10–15 days until colonies of the transformed Dunaliella Salina emerged.

What is claimed is:

1. A transgenic Dunaliella Salina bioreactor comprising: Dunaliella Salina transformed to provide transgenic Dunaliella Salina with a foreign target gene comprising a tumor necrosis factor (TNF) and a selectable marker selected from the group consisting of the aadA gene encoding spectinomycin or streptomycin, and a BAR gene encoding herbicide phosphinothricin (PPT) resistance.

2. A method for preparing a transgenic Dunaliella Salina bioreactor comprising the following steps:
(a) transforming the cells of Dunaliella Salina to provide transgenic Dunaliella Salina by introducing into the cells of Dunaliella Salina an expression vector comprising a foreign target gene comprising a tumor necrosis factor gene, together with a selectable marker selected from the group consisting of the aadA gene encoding spectinomycin or streptomycin resistance, and a BAR gene encoding herbicide phosphinothricin (PPT) resistance, to produce the Dunaliella Salina expression vector; and
(b) screening the cells of transgenic Dunaliella Salina for expression of the selectable marker, showing transformation and expression of the foreign target gene.

3. The method of claim 2 wherein the Dunaliella Salina expression vector comprises the Dunaliella Salina chloroplast atpA 5' promoter sequence and the rbcL 3'terminator sequence.

* * * * *

SEQUENCE LISTING

<160> NUMBER OF SEQ ID NOS: 6

<210> SEQ ID NO 1
<211> LENGTH: 23
<212> TYPE: DNA
<213> ORGANISM: Artificial Sequence
<220> FEATURE:
<223> OTHER INFORMATION: Description of Artificial Sequence: SYNTHETIC
      PRIMER- SENSE; DERIVED FROM HBsAg

<400> SEQUENCE: 1
gcagtcgacc caatggagag cac                                           23

-continued

```
<210> SEQ ID NO 2
<211> LENGTH: 23
<212> TYPE: DNA
<213> ORGANISM: Artificial Sequence
<220> FEATURE:
<223> OTHER INFORMATION: Description of Artificial Sequence: SYNTHETIC
      PRIMER- SENSE; DERIVED FROM HBsAg

<400> SEQUENCE: 2
gcgggtacca ggaatgtata ccc                                              23

<210> SEQ ID NO 3
<211> LENGTH: 23
<212> TYPE: DNA
<213> ORGANISM: Artificial Sequence
<220> FEATURE:
<223> OTHER INFORMATION: Description of Artificial Sequence: SYNTHETIC
      PRIMER- SENSE; DERIVED FROM HBsAg

<400> SEQUENCE: 3
ctgggtaccc caaatcctct ggg                                              23

<210> SEQ ID NO 4
<211> LENGTH: 22
<212> TYPE: DNA
<213> ORGANISM: Artificial Sequence
<220> FEATURE:
<223> OTHER INFORMATION: Description of Artificial Sequence: SYNTHETIC
      PRIMER- SENSE; DERIVED FROM HBsAg

<400> SEQUENCE: 4
gcggcatgct tagttggggt tg                                               22

<210> SEQ ID NO 5
<211> LENGTH: 29
<212> TYPE: DNA
<213> ORGANISM: Artificial Sequence
<220> FEATURE:
<223> OTHER INFORMATION: Description of Artificial Sequence: SYNTHETIC
      PRIMER-SENSE; DERIVED FROM CHOLERA TOXIN B

<400> SEQUENCE: 5
gcgggatcca tgattaaatt aaaatttgg                                        29

<210> SEQ ID NO 6
<211> LENGTH: 30
<212> TYPE: DNA
<213> ORGANISM: Artificial Sequence
<220> FEATURE:
<223> OTHER INFORMATION: Description of Artificial Sequence: SYNTHETIC
      PRIMER-ANTISENSE; DERIVED FROM CHOLERA TOXIN B

<400> SEQUENCE: 6
gcggtcgaca ggatttgcca tactaattgc                                       30
```